(12) United States Patent
Kamoda et al.

(10) Patent No.: US 6,444,703 B1
(45) Date of Patent: *Sep. 3, 2002

(54) **CYCLOHEXANE CARBOCYCLIC ESTER DERIVATIVE AND CYCLODEXTRIN COMPLEX AND COMPOSITION FOR TREATMENT OF *HELICOBACTER PYLORI* INFECTIONS**

(75) Inventors: Osamu Kamoda; Toshiharu Yanagi; Eiji Tamaki; Seiji Sato; Jun-ichi Mizoguchi, all of Hyogo (JP)

(73) Assignee: Teikoku Chemical Industries Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/091,588

(22) PCT Filed: Dec. 20, 1996

(86) PCT No.: PCT/JP96/03723

§ 371 (c)(1),
(2), (4) Date: Aug. 12, 1998

(87) PCT Pub. No.: WO97/23207

PCT Pub. Date: Jul. 3, 1997

(30) Foreign Application Priority Data

Dec. 22, 1995 (JP) ............................................... 7-354660

(51) Int. Cl.[7] .......................... A61K 31/24; A61K 47/40
(52) U.S. Cl. ........................................ 514/553; 514/58
(58) Field of Search .................................... 514/58, 553

(56) References Cited

FOREIGN PATENT DOCUMENTS

| EP | 078 599 | * | 5/1983 | |
| EP | 0 585 130 A2 | | 3/1994 | |
| EP | 0 775 692 A | | 5/1997 | .......... A61K/31/34 |
| JP | 45454/81 | | 4/1981 | |
| JP | 92260/81 | | 7/1981 | |
| JP | 92261/81 | | 7/1981 | |
| JP | 16855/82 | | 1/1982 | |
| JP | 16856/82 | | 1/1982 | |
| JP | 21360/82 | | 2/1982 | |
| JP | 75921/82 | | 2/1982 | |
| JP | 48958/82 | | 3/1982 | |
| JP | 48959/82 | | 3/1982 | |
| JP | 48960/82 | | 3/1982 | |
| JP | 75920/82 | | 5/1982 | |
| JP | 75922/82 | | 5/1982 | |
| JP | 35556/82 | | 7/1982 | |
| JP | 122059/82 | | 7/1982 | |
| JP | 122060/82 | | 7/1982 | |
| JP | 122061/82 | | 7/1982 | |
| JP | 122062/82 | | 7/1982 | |
| JP | 126461/82 | | 8/1982 | |
| JP | 126462/82 | | 8/1982 | |
| JP | 126463/82 | | 8/1982 | |
| JP | 54/87 | | 1/1987 | |
| JP | 30462/88 | | 2/1988 | |
| JP | 218652/88 | | 9/1988 | |
| JP | 217950/82 | | 8/1992 | |
| JP | 197256/82 | | 12/1992 | |
| JP | 80548/94 | | 3/1994 | |
| JP | 80549/94 | | 3/1994 | |
| JP | 80550/94 | | 3/1994 | |
| WO | 95/25513 | * | 3/1994 | |
| WO | 96/06825 | * | 3/1996 | |

OTHER PUBLICATIONS

Y. Nozawa et al., "Effects of Powder Roll Mixing to Cyclodextrin Molecular Complexation", Funsai, vol. 36, 37–44 (1992).

N.M. Sanghavi, et al., "Solubilization of Glibenclamide with β–Cyclodextrin & Its Derivatives", Drug Development And Industrial Pharmacy, 20(7), 1275–1283 (1994).

A. Marini, et al., "Thermoanalytical and Spectroscopic Characterization of β–Cyclodextrin/Ketoprofen Inclusion Complexes", J. of Inclusion Phenomena and Molecular Recognition in Chemistry, 22, 221–234 (1995).

H. Hirai, et al., "Conformation of β–Cyclodextrin–Aromatic Carboxylate Inclusion Complex in Aqueous Solution", Polymer J., vol. 28, No. 1, 91–94 (1996).

H.O. Ammar, et al., "Improvement of Some Pharmaceutical Properties of Drugs by Cyclodextrin Complexation", Phamazie, 50, 408–410 (1995).

* cited by examiner

Primary Examiner—Rebecca Cook
(74) Attorney, Agent, or Firm—Peter F. Corless; Christine C. O'Day; Edwards & Angell, LLP (57) ABSTRACT

The present invention relates to a pharmaceutical composition which is appropriate for eradication or extermination of *Helicobacter pylori* wherein [4-[4-(4-methylbenzyloxycarbonyl)phenyl[phenyl trans-4-guanidinomethylcyclohexanecarboxylate or an acid addition salt thereof are compounded and it also relates to a complex consisting them.

7 Claims, 7 Drawing Sheets

CYCLOHEXANE CARBOCYCLIC ESTER DERIVATIVE AND CYCLODEXTRIN COMPLEX AND COMPOSITION FOR TREATMENT OF *HELICOBACTER PYLORI* INFECTIONS

This is a 371 of PCT/JP96/03723 filed Dec. 20, 1996.

TECHNICAL FIELD

The present invention provides a pharmaceutical composition which is effective for eradication *Helicobacter pylori* living in human stomach and, accordingly, said invention is utilized in the medical field.

The present invention also provides a complex of 4-[4-(4-methylbenzyloxycarbonyl)phenyl]phenyl trans-4-guanidinomethylcyclohexanecarboxylate or an acid addition salt thereof with β-cyclodextrin.

BACKGROUND ART

*Helicobacter pylori* is a bacterium which has recently attached considerable attention in view of its relationship with diseases of digestive organs. It has become an important factor to be taken into consideration especially when diseases, particularly ulcer, of stomach and duodenum is investigated.

As the drugs effective for inhibiting the growth of *Helicobacter pylori* antibiotic substances such as ampicillin, amoxicillin, caphalexin and clarithromycin and synthetic antibacterials such as ofloxacin and ciprofloxacin have been known. It has been clarified that *Helicobacter pylori* has participated in recurrence of ulcer and, at the same time, prevention of recurrence of ulcer by a combined use of those antibacterials with antiulcer agent has been investigated.

Incidentally, when anitiobiotics or synthetic antibacterials are administered, they are absorbed from digestive organs into blood and arrive at the diseased site to achieve the effect while some of them are excreted after passing through the digestive organs and, when the drug passes through the intestinal tract, many bacteria living in intestine are killed whereby enterobacterial fleora is unbalanced. Accordingly, administration of such a drug for long term is to be avoided.

Since *Helicobacter pylori* is a bacterium living in stomach, there has been a demand for a compound having a property that its activity to said bacterium is effectively achieved in stomach and, after that, the antibacterial activity decreases when it moves to duodenum and then to small intestine and finally said activity disappears. Incidentally, there is a compound whose generic name is benexate hydrochloride and it has been known that said compound has an anti-*Helicobacter pylori* activity with MICs ranging from 25 to 50 µg/ml ("Diseases of Digestive Organs and *Helicobacter pylori*", page 91; published by Medical Review).

The present applicant previously found a compound showing an effective antibacterial activity which is specific to *Helicobacter pylori* although it was a result of the test in vitro (WO 96/06825) and, in view of the fact that the result in vivo does not always coincide with that in vitro. The mode of its use was investigated whereby the present invention has been achieved.

DISCLOSURE OF THE INVENTION

The present invention is to provide a composition of 4-[4-(4-methylbenzyloxycarbonyl)phenyl]phenyl trans-4-guanidinomethylcyclohexanecarboxylate or an acid addition salt thereof (hereinafter, it will be referred to as "the present compound") which is suitable for exterminating or eradicating *Helicobacter pylori* in living body by the use of the present compound.

It has been known that, although the present compound exhibits an antibacterial action quite specifically to *Helicobacter pylori* according to an in vitro test (WO 96/06825), such an antibacterial activity in vitro is not available in an in vivo test as it is. As one of the causes, we took the solubility of the present compound into consideration but, after various investigations, it has been found that an improvement in solubility only is not able to afford the effect of eradication or extermination of *Helicobacter pylori* and, at the same time, we have found that a combined use of the present compound with cyclodextrin, particularly with β-cyclodextrin, is effective in eradication or extermination of *Helicobacter pylori* in living body whereupon the present invention has been achieved.

The present invention provides a pharmaceutical composition having an anti-*Helicobacter pylori* action which contains 4-[4-(4-methylbenzyloxycarbonyl)phenyl]phenyl trans-4-guanidinomethylcyclohexanecarboxylate or an acid addition salt thereof and β-cyclodextrin.

The present invention also provides a complex of 4-[4-(4-methyl-benzyloxycarbonyl)phenyl]phenyl trans-4-guanidinomethylcyclohexanecarboxylate or an acid addition salt thereof with β-cyclodextrin.

The composite which is an object of the present invention is also an effective component of the pharmaceutical composition of the present invention and it consists of the present compound and β-cyclodextrin and may be prepared by grinding the two substances or by making them an aqueous solution followed by subjecting to a treatment of spray-drying, freeze-drying or drying by means of concentration.

Further, even In the case where they are just mixed, it is effective in eradication or extermination of *Helicobacter pylori* which is an object of the present invention provided that said mixture is dissolved in water. Therefore, such a mixture is covered by the present invention as well.

Accordingly, the present invention provides a mixture or a complex (inclusion compound) of 4-[4-(4-methylbenzyloxycarbonyl)phenyl]phenyl trans-4-guanidinomethylcyclohexane carboxylate or an acid addition salt thereof and β-cyclodextrin and also offers a composition containing the same which has an anti-*Helicobacter pylori* action.

BEST MODES FOR CONDUCTING THE INVENTION

The present compound has been known already (WO 96/06825) and can be manufactured by a known method. For example, 4-methylbenzyl 4-(4-hydroxyphenyl)benzoate is prepared by a conventional method from 4-(4-hydroxyphenyl)benzoic acid and 4-methylbenzyl bromide and is made to react with trans-4-guanidinomethylcyclohexanecarboxylic acid or a reactive derivative thereof to give the present compound.

In addition, the present compound may be used as an acid addition salt if necessary. Examples of the preferred salt are salts with pharmaceutically acceptable organic and inorganic acids such as hydrochloric acid, methanesulfonic acid, toluenesulfonic acid, fumaric acid, oxalic acid, hydrobromic acid and sulfuric acid.

With regard to cyclodextrin, that which is commercially available may be used. Among the cyclodextrin, the use of β-cyclodextrin is particularly preferred. The amount of the cyclodextrin used is 0.5–10 mole, preferably 1–4 moles or, more preferably, 1–3 moles to one mole of the present compound. When the molar ratio of cyclodextrin is less than 0.5, solubility decreases and the chemical stability of the present compound which is a main ingredient in a state of solution lowers. When the amount of cyclodextrin used is too much, the content of the main ingredient per unit weight becomes small whereby total amount to be administered for giving a certain amount of the main ingredient becomes large and that is not preferred.

The pharmaceutical composition of the present invention is characterized in containing a complex of the present compound with cyclodextrin, particularly with β-cyclodextrin. If necessary, various components and vehicles may be further added to the pharmaceutical composition of the present invention.

The pharmaceutical composition of the present invention may be made into a dosage form which is suitable for administration by adding the above-mentioned compounded product and, if necessary, various components and vehicles.

The compounded product of the present invention is offered as powder which is prepared by grinding the mixture of the present compound and β-cyclodextrin in a ball mill device or prepared by dissolving it in water with warming or by dissolving the present compound by adding to β-cyclodextrin dissolved in water with warming followed by subjecting the resulting solution to concentrating in vacuo, freeze-drying or spray-drying for solidification.

Among the compounded product in accordance with the present invention, chemical structure of the product prepared by grinding with a ball mill device or the complex of the present compound with β-cyclodextrin obtained by dissolving with warming followed by solidifying has not been definitely clarified but it will be understood from the data of the physical properties measured which will be mentioned later that the present compound and β-cyclodextrin act each other forming a united state (such as an inclusion compound).

Figure 1:
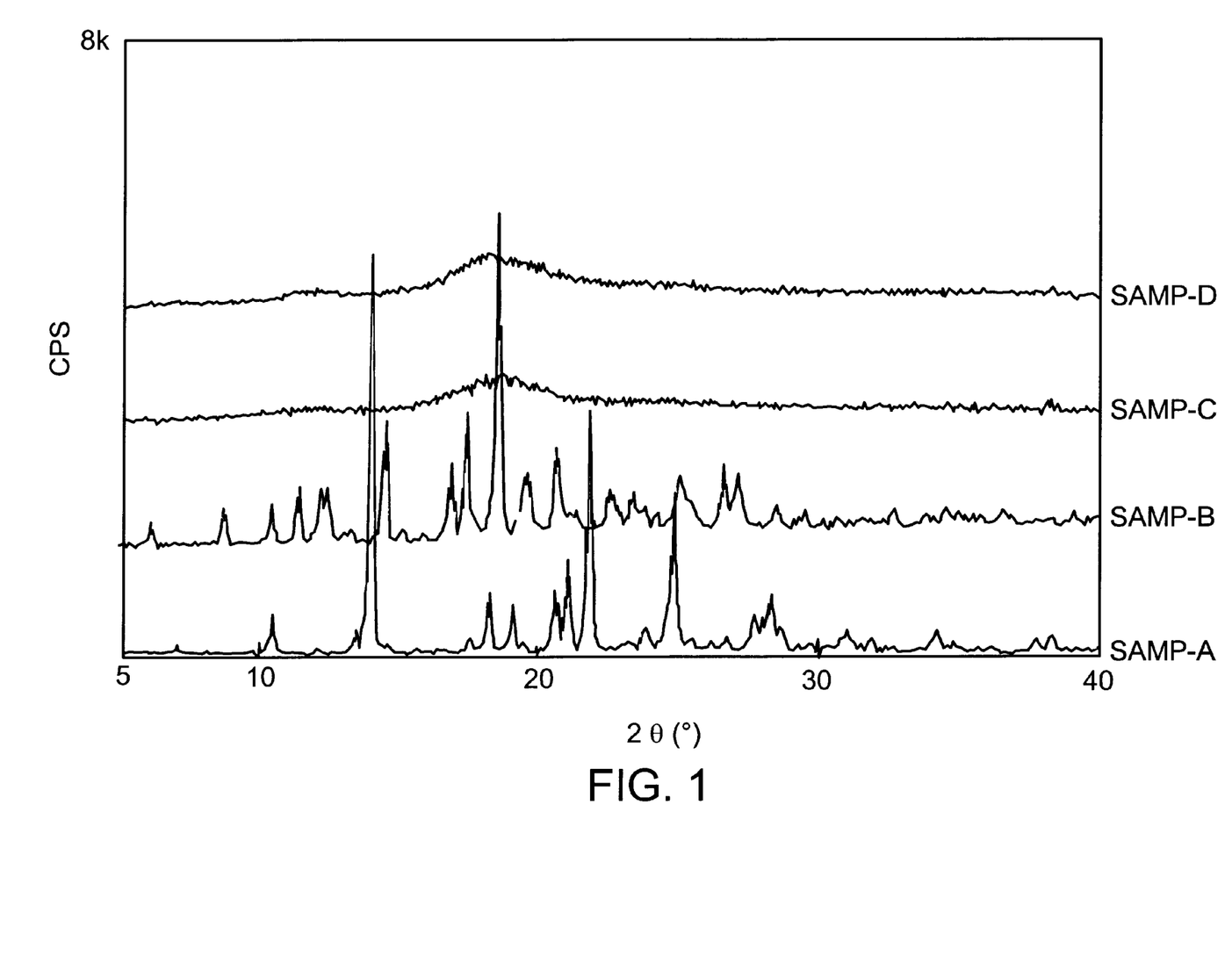
FIG. 1 shows the diffraction peak of the powder X-ray diffraction of the complex of the present invention. The charts of SAMP-C and SAMP-D in FIG. 1 are those for the complex of the present invention, that of SAMP-B is for β-cyclodextrin and that of SAMP-A is for a hydrochloride of the present compound.

Thus, as shown in FIG. 1 where charts of results of powder X-ray diffraction of the hydrochloride of, the present compound (SAMP-A). β-cyclodextrin (SAMP-B) and the complex of the present invention (SAMP-C and SAMP-D) are given, it is apparent that there is no diffraction peak derived from crystals of the present compound and of β-cyclodextrin in the case of the complex of the present invention, that they are in an amorphous form in the complex of the present invention and accordingly that there is a clear difference between the two.

Figure 2:
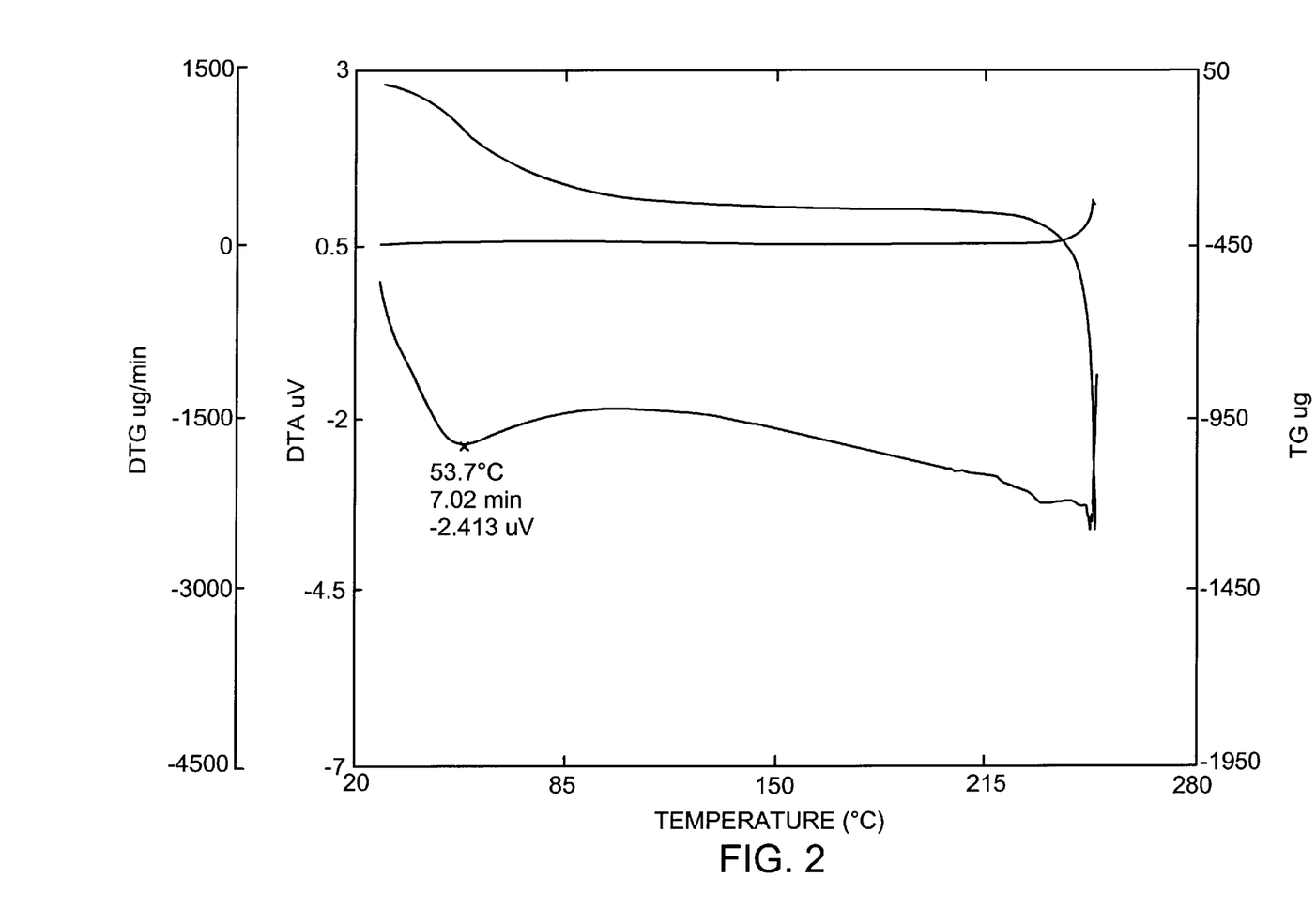
FIG. 2 shows the result of the thermogravimetric differential thermal analysis of the complex of the present invention.
Figure 3:
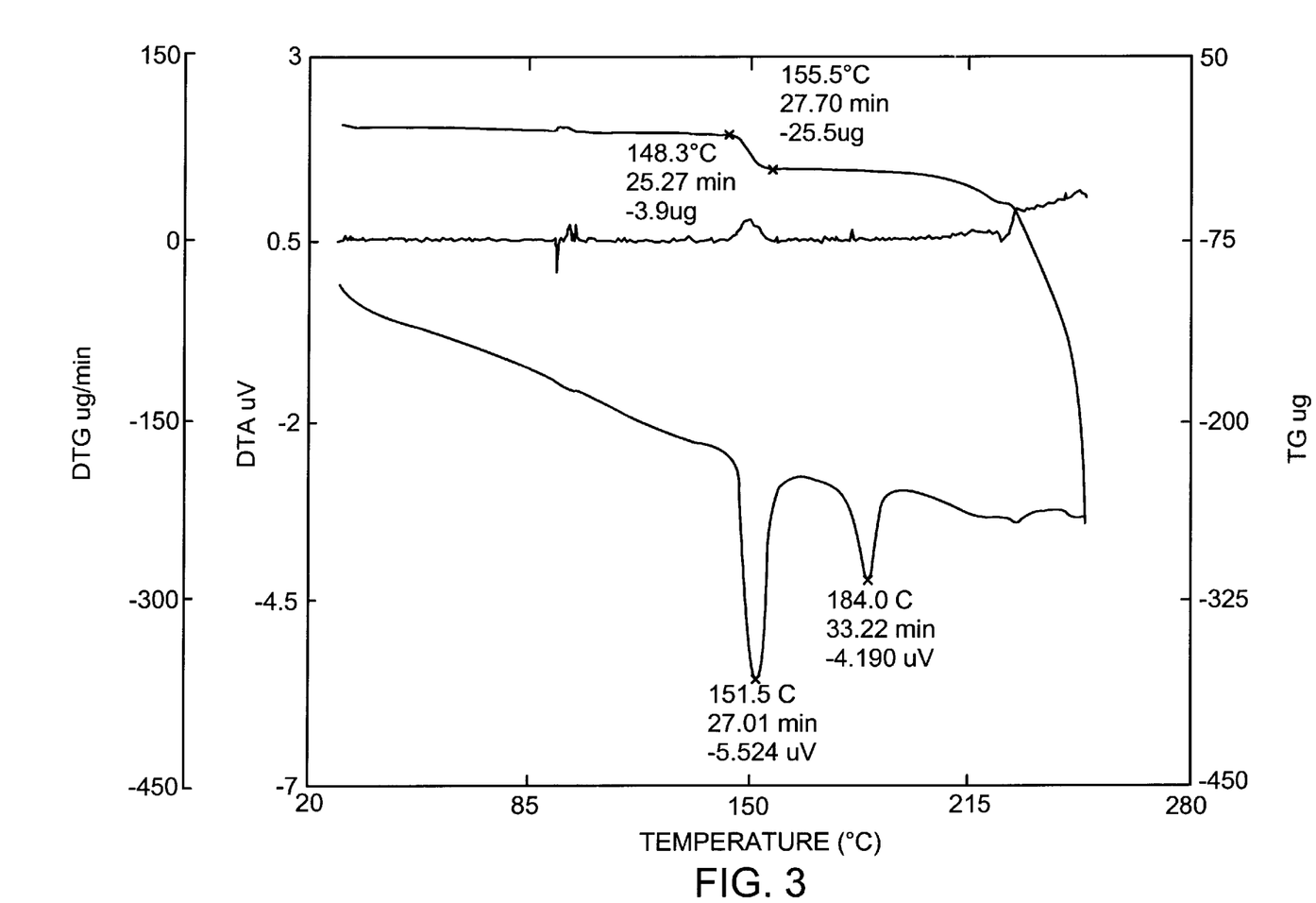
FIG. 3 shows the result of the thermogravimetric differential thermal analysis of the present compound (hydrochloride).
Figure 4:
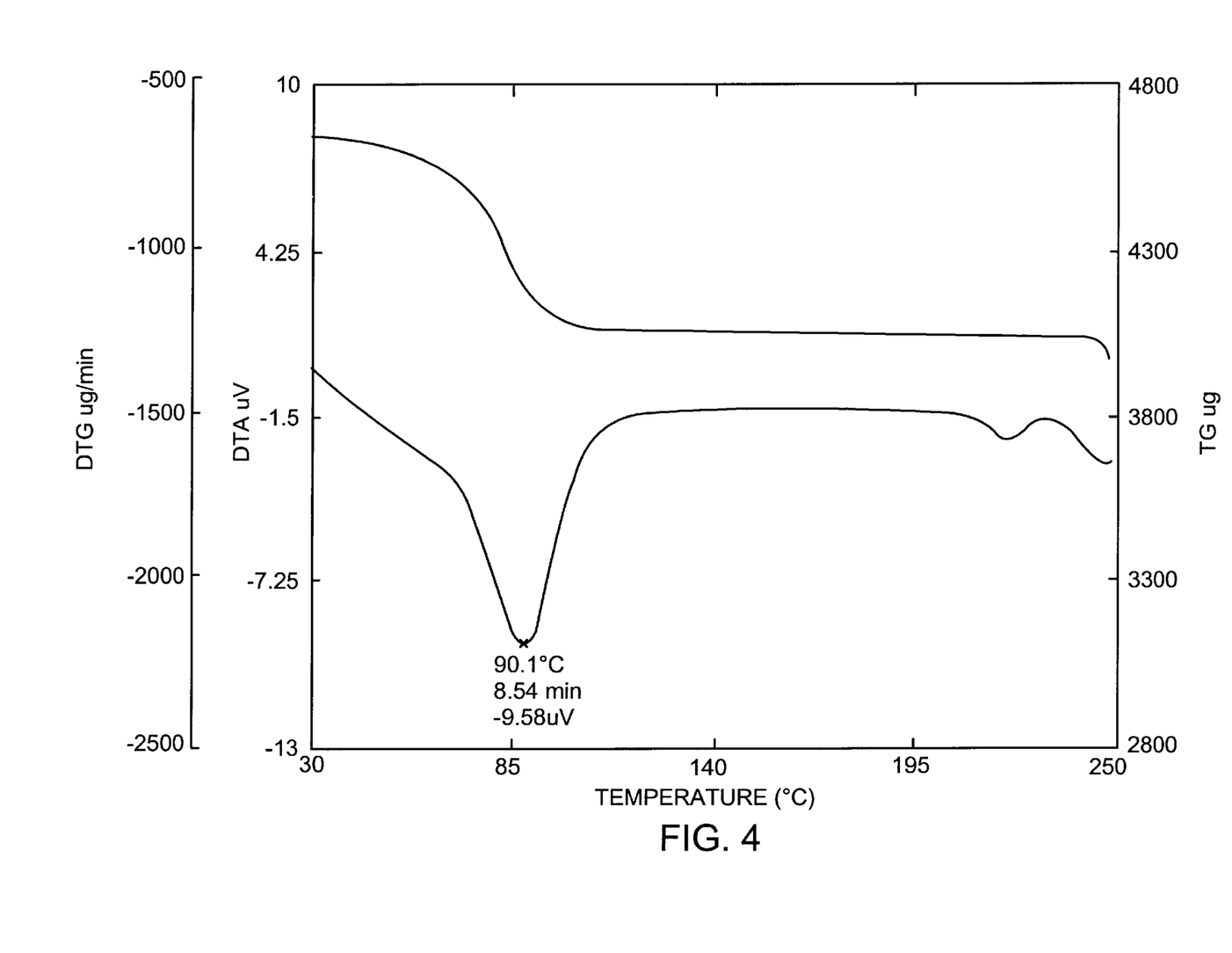
FIG. 4 shows the result of the thermogravimetric differential thermal analysis of β-cyclodextrin.
Figure 5:
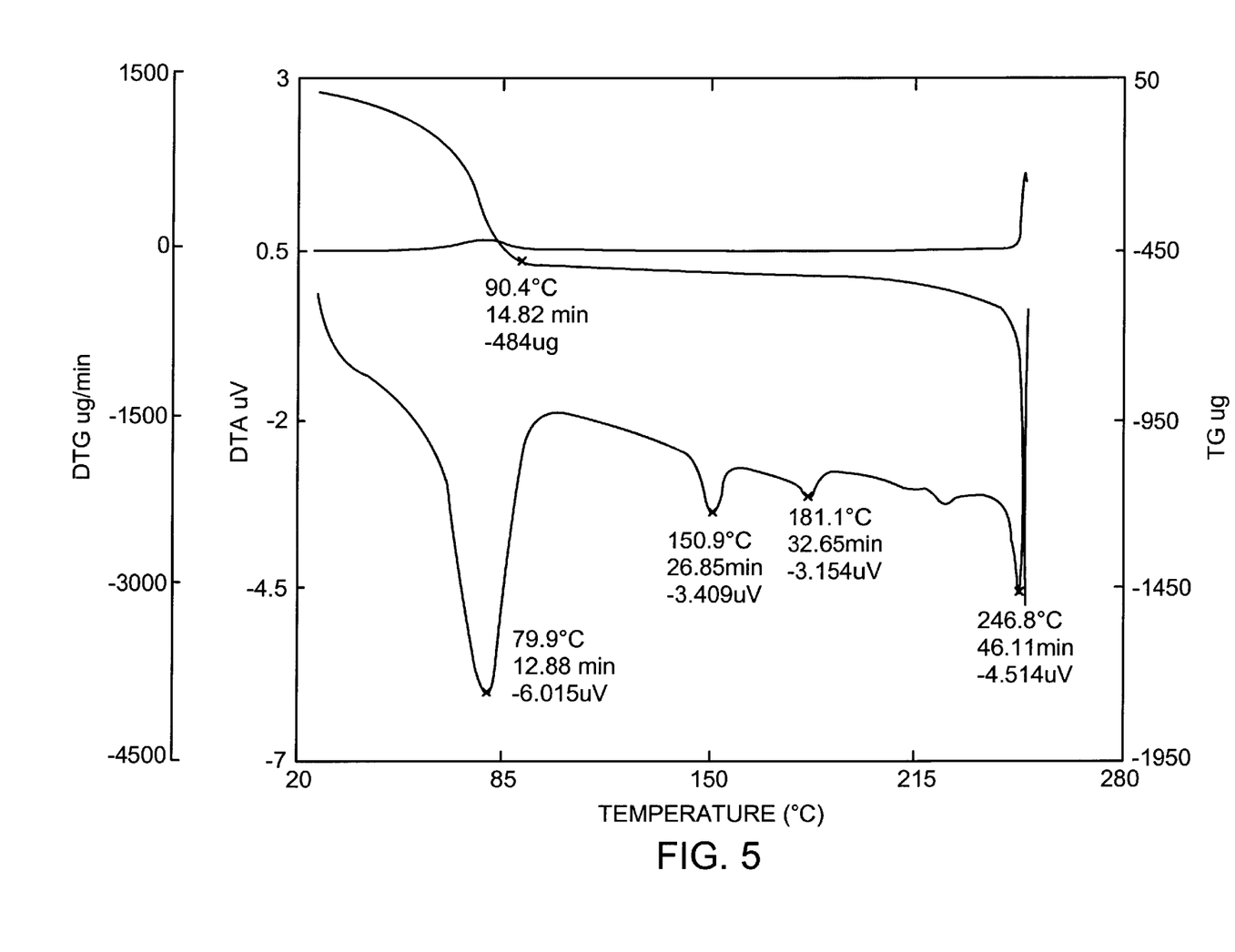
FIG. 5 shows the result of the thermogravimetric differential thermal analysis of a mere 1:1 mixture of the present compound (hydrochloride) with β-cyclodextrin.

Further, as shown in FIGS. 2–5 where the result of thermogravimetric differential thermal analysis of the complex of the present invention (FIG. 2), that of the present compound (FIG. 3), that of β-cyclodextrin (FIG. 4), and that of a mere mixture of the present compound and β-cyclodextrin (FIG. 5) are given, the present compound shows endothermic peaks at 151.5° C. and 184.0° C. (FIG. 3), β-cyclodextrin shows an endothermic peak at 90.1° C. (FIG. 4; incidentally, in FIG. 4, a loss curve per minute in the center of the figure as seen in FIGS. 2, 3 and 5 is not shown), and a mere mixture of them shows endothermic peaks at the three points corresponding to the components thereof (FIG. 5). On the contrary, the complex of the present invention shows only a gentle and single endothermic peak at 53.7° C. whereby it is apparent from the results of thermogravimetric differential thermal analysis that the complex of the present invention is not a mere mixture but is a complex wherein both act each other.

Figure 6:
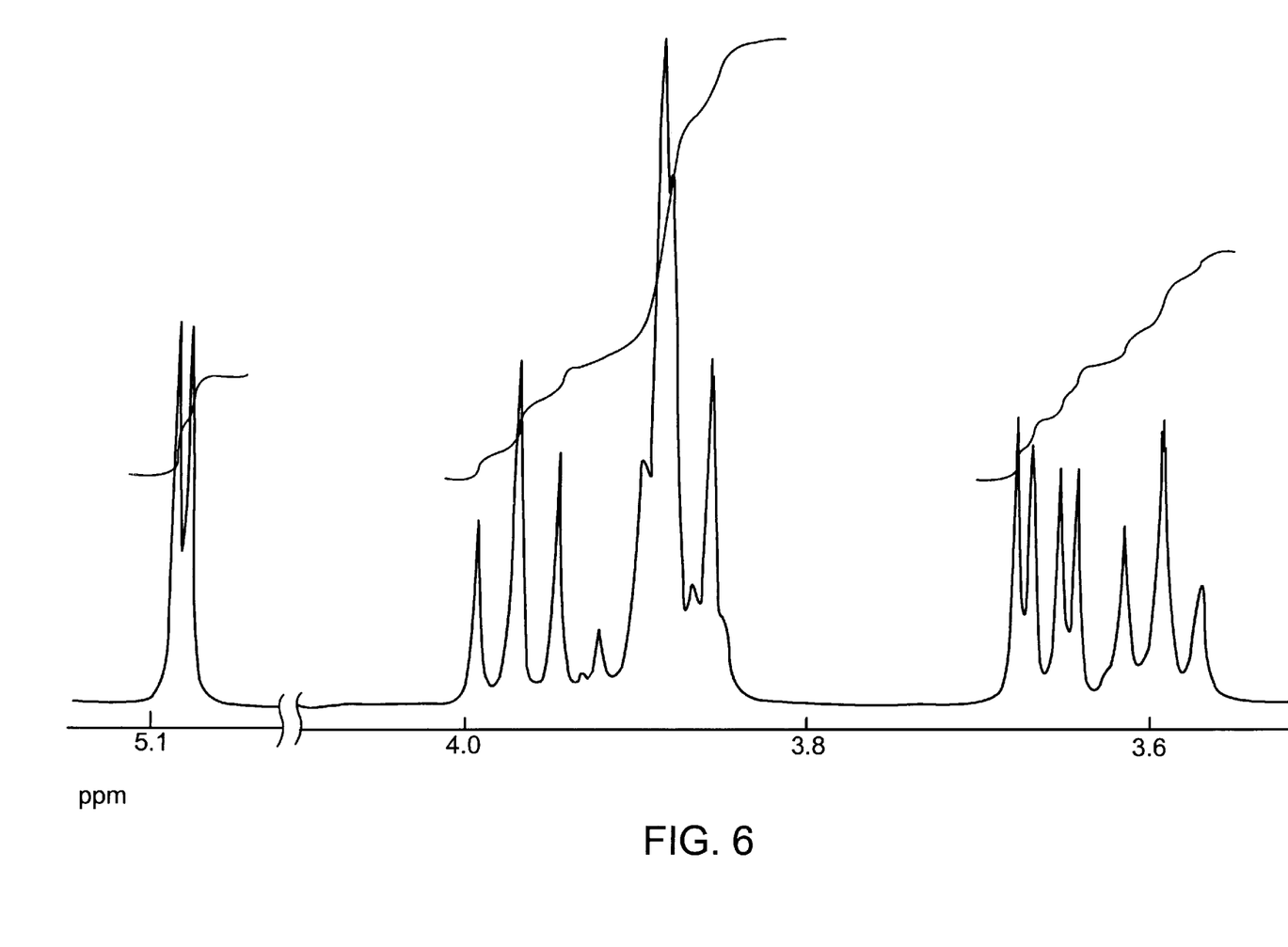
FIG. 6 shows a nuclear magnetic resonance spectrum of hydrogen atoms which are directly bonded to carbon atoms of β-cyclodextrin.
Figure 7:
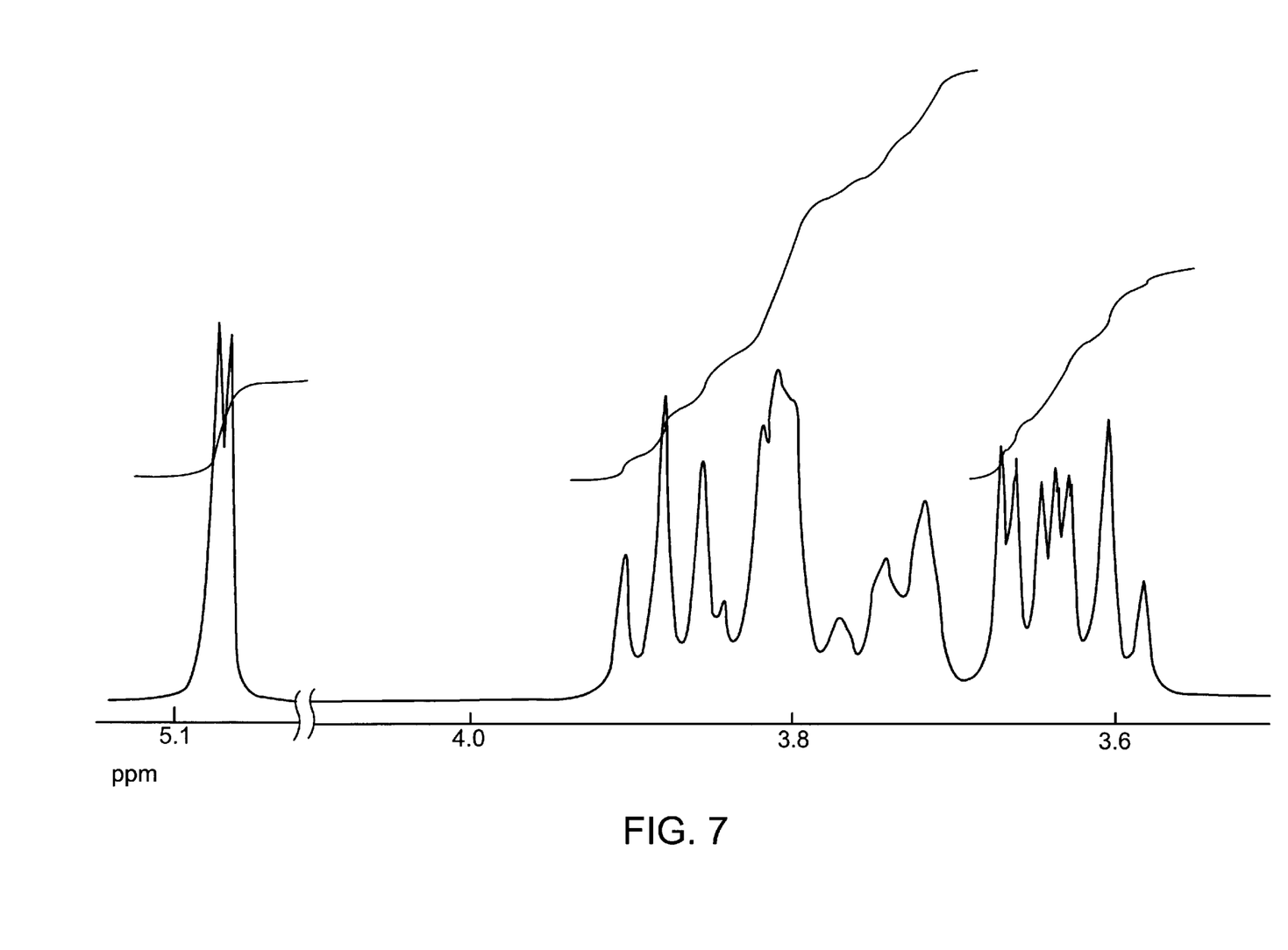
FIG. 7 shows a nuclear magnetic resonance spectrum of hydrogen atoms which are directly bonded to carbon atoms of a β-cyclodextrin moiety in the complex of the present invention.

Further, in FIGS. 6–7, nuclear magnetic resonance spectrum of hydrogen atoms which are directly bonded to carbon atoms of β-cyclodextrin (FIG. 6) and that of hydrogen atoms at the same positions of the complex of the present invention (FIG. 7) are shown. The thing which is to be particularly noted in the spectra is the peak which appears at 3.8–4.0 ppm and that is the characteristic values of hydrogen atoms bonded to carbon atoms of 3-, 5- and 6-positions of β-cyclodextrin.

In the complex of the present invention, said characteristic value is shifted to the higher magnetic field side to an extent of 0.1 ppm and is available at 3.7–3.9 ppm and said fact supports that there is an interaction between the present complex and β-cyclodextrin.

As such, it is believed that the complex of the present invention is not a mere mixture of the present compound and β-cyclodextrin but is a complex wherein both act each other.

The present invention will be further illustrated by way of specific examples as hereunder although the present invention is not limited thereto.

Referential Example

Manufacture of the Present Compound

4-[4-(4-Methylbenzyloxycarbonyl)phenyl]phenyl trans-4-guanidinomethylcyclohexanecarboxylate hydrochloride which is used in the present invention was synthesized as follows. Thus, 1.11 g of thionyl chloride was dropped into a mixture of 5.95 g of 4-methylbenzyl 4-(4-hydroxyphenyl) benzoate [m.p. 128–130° C.; which was synthesized by a conventional method from 4-(4-hydroxyphenyl)benzoic acid and 4-methylbenzyl bromide], 1.48 g of pyridine and 30 ml of dry tetrahydrofuran under ice-cooling. This was stirred for three hours at room temperature, crystals separated out therefrom were filtered off and the filtrate was concentrated in vacuo. Dry pyridine (30 ml) was added thereto, the mixture was cooled with ice and 2.00 g of trans-4-guanidinomethylcyclohexanecarboxylic acid hydrochloride was added thereto. The mixture was stirred overnight at room temperature and concentrated in vacuo and the crystals separated out therefrom by addition of acetone were collected by filtration and well washed with isopropanol to give 4-[4-(4-Methylbenzyloxycarbonyl)phenyl]phenyl trans-4-guanidinomethylcyclohexanecarboxylate hydrochloride.

Yield: 3.19 g.

m.p.: 171–173° C.

A. Preparation of Drugs to be Tested and Solution to be Administered

Example 1

β-Cyclodextrin (8.469 g) was dissolved in 120 ml of water with warming, 4 g of the present compound (hydrochloride) was added thereto (molar ratio thereof being 1:1) and the mixture was heated at 60–70° C. for one hour to dissolve. This was freeze-dried.

Solubility of this product at 25° C. was as follows.

In water; 408 µg/ml

In the first fluid (The Japanese Pharmacopoeia) (pH 1.2): 9 µg/ml

In 0.1M acetate buffer (pH 4.0): 158 µg/ml

In 0.05M phosphate buffer (pH 6.5): 9 µg/ml

This was dissolved in distilled water with warming to make the amount of the present compound (hydrochloride) 100 mg/10 ml and subjected to administration.

Example 2

The present compound (hydrochloride) (100 mg) and 212 mg of β-cyclodextrin were dissolved in 10 ml of distilled water with warming and subjected to administration.

Example 3

The mixture of the present compound (hydrochloride) (5 g) and 11.7 g of β-cyclodextrin (molar ratio being 1:1) was graund for seven hours using CENTRIFUGAL BALL MILL (manufactured by Retsch) under the conditions where three balls were used and speed scale was adjusted to 70.

The resulting powder was subjected measurements for powder X-ray diffraction and thermogravimetric differential thermal analysis and the state was investigated.

The data were compared with those of the present compound per se, β-cyclodextrin and a mere 1:1 mixture (molar ratio) of them.

In the powder X-ray diffraction, no diffraction peak derived from the crystals of the present compound was noted and, therefore, it is apparent that the present invention was made into amorphous (refer to FIG. 1).

In the infrared absorption spectrum, the characteristic absorptions derived from the two types of ester bond near $1742 cm^{-1}$ and $1702 cm^{-1}$ noted in the present compound moved to the higher wave number side. This shows that some physicochemical interaction took place between the present compound and β-cyclodextrin.

It was further noted by the thermogravimetric differential thermal analytical data that the endothermic peaks shown in FIGS. 3–5 which were noted in the present compound per se (FIG. 3), β-cyclodextrin (FIG. 4) and a mere mixture (molar ratio being 1:1) of them (FIG. 5) disappeared in the powder resulted here (refer to FIG. 2). In addition, almost no change was noted in hydrogen atom signals at the positions of $C_1$, $C_2$ and $C_4$, in the nuclear magnetic resonance spectrum ($^1H$ resonance frequency: 400 MHz; concentration for the measurement: 2.8 mmol/liter; solvent: heavy water; external standard substance: TSP; temperature for the measurement: 303° K.). On the other hand, the hydrogen atom signals which are the characteristic values for β-cyclodextrin appearing at 3.8–4.0 ppm for $C_3$, $C_5$ and $C_6$ derived from the hexose structure shifted to 3.7–3.9 ppm. When the bonding direction of hydrogen atoms at the above-mentioned positions in hexose which constitutes β-cyclodextrin is taken into consideration, such a change in said spectrum strongly suggests that inclusion takes place between β-cyclodextrin and the present compound.

Solubility of this product in water was 4 mg/ml (25° C.).

The product was dissolved in distilled water to make the content of the present compound (hydrochloride) 100 mg/10 ml and subjected to administration.

Example 4

The present compound (hydrochloride) (4 g) and 18.7 g of β-cyclodextrin (molar ratio being 1:2) were treated by the same manner as in Example 3 to give powder. The resulting powder showed the same physical property as that of the powder of Example 3 except the solubility (8.9 mg/ml).

The resulting powder was dissolved in distilled water to make the content of the present compound (hydrochloride) 100 mg/ml and subjected to administration.

Example 5

The present compound (2 g) and 18.7 g of β-cyclodextrin (molar ratio being 1:4) were treated by the same manner as in Example 3 to give powder. The resulting powder showed the same physical property as that of the powder of Example 3 except the solubility (9.4 mg/ml).

The resulting powder was dissolved in distilled water to make the content of the present compound (hydrochloride) 100 mg/ml and subjected to administration.

Example 6

The present compound (2 g) and 14.0 g of β-cyclodextrin (molar ratio being 1:3) were dissolved in 200 ml of warm water and spray-dried (temperature at inlet: 130° C.; air flow rate: 6 ml/minute) to give powder. The resulting powder showed the same physical property as that of the powder of Example 3 except the solubility (8.0 mg/ml).

The resulting powder was dissolved in distilled water to make the content of the present compound (hydrochloride) 100 mg/ml and subjected to administration.

Example 7

γ-Cyclodextrin (9.678 g) was dissolved in 100 ml of water with warming, 4 g of the present compound (hydrochloride) was added to the resulting solution (molar ratio being 1:1) and the mixture was heated at 60–70° C. for one hour followed by freeze-drying.

Solubility of the product at 25° C. was as follows.

In water: 729 µg/ml

In the first fluid (The Japanese Pharmacopoeia) (pH 1.2) 15 µg/ml

In 0.1M acetate buffer (pH 4.0): 431 µg/ml

In 0.05M phosphate buffer (pH 6.5): 2 µg/ml

This was dissolved in distilled water with warming to make the amount of the present compound (hydrochloride) 100 mg/10 ml and subjected to administration.

Example 8

The present compound (hydrochloride) (2 g) and 14.0 g of β-cyclodextrin (molar ratio being 1:3) were treated by the same manner as in Example 3 to give powder. The resulting powder showed the same physical property as that of the powder of Example 3 except the solubility (9.0 mg/ml).

The resulting powder was dissolved in distilled water to make the content of the present compound (hydrochloride) 100 mg/ml and subjected to administration.

Comparative Example 1

The present compound (hydrochloride) per se was administered as well and Its solubility at 25° C. was as follows.

In waters 24 μg/ml

In the first fluid (The Japanese Pharmacopoeia) (pH 1.2): <0.1 μg/ml

In 0.1M acetate buffer (pH 4.0): <0.1 μg/ml

In 0.05M phosphate buffer (pH 6.5): <0.1 μg/ml

This was dissolved in distilled water containing 0.5% of methyl cellulose to make the content of the present compound (hydrochloride) 100 mg/ml and subjected to administration.

Comparative Example 2

A mixture of 3 g of the present compound (hydrochloride) and 6 g of polyvinylpyrrolidone K30 was dissolved in methanol and the solution was evaporated to dryness in vacuo to give powder. Its solubility at 25° C. was as follows.

In water: 761 μg/ml

In the first fluid (The Japanese Pharmacopoeia) (pH 1.2): 253 μg/ml

In 0.1M acetate buffer (pH 4.0): 320 μ/ml

In 0.05M phosphate buffer (pH 6.5): 2 μg/ml

This was dissolved in distilled water to make the content of the present compound (hydrochloride) 100 mg/ml and subjected to administration.

Incidentally, the method for measuring the solubility in each example is as follows. Thus, an excessive amount of the present compound was added to a certain amount of solvent, the mixture was shaken for one hour, the supernatant liquid was removed and the amount of the present compound contained therein was measured wherefrom the solubility was calculated.

TEXT EXAMPLE (1) Preparation of Animals Infected by *Helicobacter pylori*

*Helicobacter pylori* ATCC 43504 (100 μl) was inoculated into Brain heart infusion broth containing 10% calf serum and incubated at 37° C. for 24 hours in a microaerophilic atmosphere. The culture broth (0.5 ml containing about $3 \times 10^8$ CFU/ml) was administered orally to Mongolian gerbils (MON/Jms/Gba Slc; male of six weeks age) after fasting for 24 hours, then neither feed nor water was given for four hours and, after that, the animals were given with feed and water for ten days.

(2) Administration of the Drug to be Tested

Three infected animals as prepared in (1) were used per group. They were fasted from 20 hours before the 11th day (although water was made freely taken by them) and, during the fasted stage, 10 ml/kg each of the test drugs for administration prepared in Examples and Comparative Examples were orally given to them at 9:00, 13:00 and 17:00 o'clock on the 11th day. Feeding was started as from 21:00 o'clock and, after 20 hours from the final administration, stomach of the animals was removed and *Helicobacter pylori* living therein was subjected to a viable cell counting.

(3) Method of Counting the Viable Cells

The stomachs were cut open and the contents were removed (no washing conducted) and homogenized in 20 ml of 0.1M phosphate buffer (pH 7.2) to give a sample for viable cell counting. This sample was diluted with 0.1M phosphate buffer (pH 7.2) (0, −1, −2, −3) each 0.1 ml thereof was smeared on a selective medium, incubated at 37° C. in a microaerophilic atmosphere. The growing colonies were counted after 6 days.

(4) Composition of the selected medium used here was as follows. Thus it consisted of 43 g of brucella agar, 100 ml of horse blood, 10 mg of vancomycin, 2500 U of polymyxin B, 5 mg of trimethoprim, 2 mg of amphotecillin B, 50 mg of 2.3,5-triphenyltetrazolium chloride and 900 ml of distilled water and its pH was 7.2±0.2.

The case where no test drug was administered was used as a control (administered only with distilled water containing 0.5% of methyl cellulose) and the resulting effect was compared with that where the test drug was administered using the eradication rate. The result is given in Table 1.

Incidentally, the eradication rate was calculated according to the following calculating expression.

Eradication Rate={[(Viable Cell Numbers in Control)−(Viable Cell Numbers in Drug-Administered Group)]/[Viable Cell Numbers in Control]}×100

The viable cell numbers in stomach of infected Mongolian gerbils in the control group were $3.7 \times 10^4$ CFU/stomach (average of three animals).

TABLE 1

Result of Measurement of Eradication Rate

| Drug Tested | | Eradication Rate (%) |
|---|---|---|
| Example 1 | 1 | 99.1 |
| | 2 | >99.9 |
| | 3 | >99.9 |
| Example 2 | 1 | 99.4 |
| | 2 | 99.4 |
| | 3 | 99.7 |
| Example 3 | 1 | 95.8 |
| | 2 | 97.2 |
| | 3 | >99.9 |
| Example 4 | 1 | 99.1 |
| | 2 | >99.9 |
| | 3 | 99.2 |
| Example 5 | 1 | 99.9 |
| | 2 | >99.9 |
| | 3 | 99.9 |
| Example 6 | 1 | >99.9 |
| | 2 | 98.2 |
| | 3 | 98.7 |
| Example 7 | 1 | 78.9 |
| | 2 | 91.4 |
| | 3 | 99.5 |
| Example 8 | 1 | 99.8 |
| | 2 | 99.3 |
| | 3 | 99.8 |
| Comp.Ex.1 | 1 | 95.7 |
| | 2 | 62.2 |
| | 3 | 0 |
| Comp.Ex.2 | 1 | 87.0 |
| | 2 | 89.2 |
| | 3 | 62.2 |

Viable cell numbers in the control: $3.7 \times 10^4$ CFU/stomach (average of three animals)

What is claimed is:

1. A pharmaceutical composition having an anti-*Helicobacter pylori* action which comprises 4-[4-(4-methylbenzyloxycarbonyl)phenyl]phenyl trans-4-guanidinomethylcyclohexanecarboxylate or an acid addition salt thereof and cyclodextrin.

2. A pharmaceutical composition according to claim 1 having anti-*Helicobacter pylori* action which comprises 4-[4-(4-methylbenzyloxycarbonyl)phenyl]phenyl trans-4-guanidinomethylcyclohexanecarboxylate or an acid addition salt thereof and cyclodextrin in a compounding ratio of 1:1–4 (molar ratio).

3. A pharmaceutical composition having an anti-*Helicobacter pylori* action which comprises a complex of 4-[4-(4-methylbenzyloxycarbonyl)phenyl]phenyl trans-4-guanidinomethylcyclohexanecarboxylate or an acid addition salt thereof and cyclodextrin.

4. A pharmaceutical composition according to any of claims 1 to 3 wherein cyclodextrin is β-cyclodextrin.

5. A complex of 4-[4-(4[methylbenzyloxycarbonyl)phenyl trans-4-guanidinomethyloyclohexanecarboxylate or an acid addition salt thereof with β-cyclodextrin.

6. A method of treating an animal having a *Helicobacter pylori* infection, comprising administering to the animal an effective amount of a pharmaceutical composition comprising 4-[4-(4-methylbenzyloxycarbonyl)phenyl]phenyl trans-4-guanidinomethylcyclohexanecarboxylate or an acid addition salt thereof and cyclodextrin.

7. The method of claim 6 wherein the cyclodextrin is β-cyclodextrin.

\* \* \* \* \*